United States Patent
Palatnik

[11] Patent Number: 5,768,166
[45] Date of Patent: Jun. 16, 1998

[54] ADAPTIVE FILTER FOR ELECTRICAL SUPPLY LINE NOISE

[75] Inventor: Eugene S. Palatnik, Pewaukee, Wis.

[73] Assignee: Biochem International, Inc., Waukesha, Wis.

[21] Appl. No.: 831,685

[22] Filed: Apr. 10, 1997

[51] Int. Cl.$^6$ ............................................. G06F 17/10
[52] U.S. Cl. ............................................. 364/724.19
[58] Field of Search .................... 364/724.19, 724.2, 364/724.09, 724.08, 724.011; 375/232

[56] References Cited

U.S. PATENT DOCUMENTS

| | | | |
|---|---|---|---|
| 4,438,504 | 3/1984 | Favin | 364/724.19 |
| 5,325,204 | 6/1994 | Scarpa | 364/724.19 |

*Primary Examiner*—Tan V. Mai
*Attorney, Agent, or Firm*—Quarles & Brady

[57] ABSTRACT

A filter system is provided to remove electrical supply line noise at a first frequency from an input signal to a medical monitor. An arithmetic unit produces an intermediate signal having a frequency component that corresponds to a difference between the first frequency and a reference frequency. A calculator determines the period of the intermediate signal and a signal converter produces a sinusoidal signal which has the period determined by the calculator. An adder produces a filter control signal having a value that represents the sum of the reference frequency and the frequency of the intermediate signal. A notch filter is employed to remove the electrical supply line noise from the input signal. The filter control signal tunes the notch filter to the first frequency of the electrical supply line noise.

12 Claims, 1 Drawing Sheet

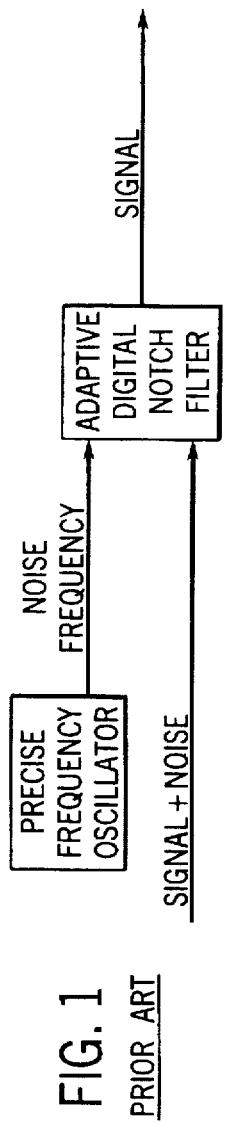
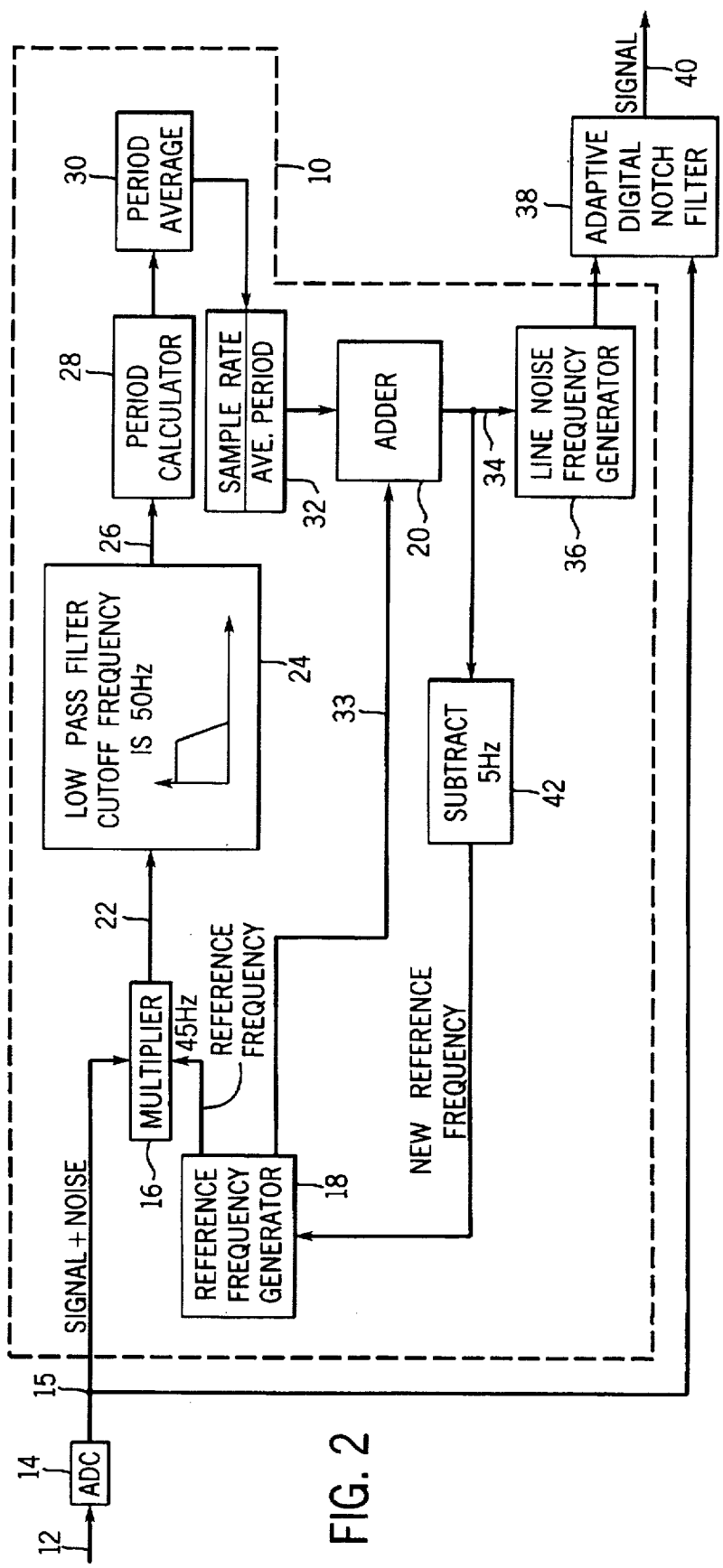
FIG. 1 PRIOR ART
FIG. 2

ADAPTIVE FILTER FOR ELECTRICAL SUPPLY LINE NOISE

BACKGROUND OF THE INVENTION

The present invention relates to filters for removing electrical supply line noise from other electrical signals; and more particularly to such filters for processing input signals in medical monitoring equipment.

The input signals for medical monitoring equipment, such as an electrocardiograph (ECG), often become corrupted by electrical noise from adjacent electrical supply lines in the building where the equipment is being used. The ECG receives input signals through a multi-conductor cable from electrodes placed on a medical patient. In many environments where the ECG is used, an electrical noise from adjacent power lines is inductively coupled to the ECG cable, thereby imposing a significant amount of electrical noise onto the weak ECG signals. The signal-to-noise ratio between the electrical supply line noise and the ECG signal can be fairly low. Furthermore, the 50 Hz or 60 Hz frequency of the electrical supply line noise is within the frequency spectrum of the ECG input signals.

As a consequence, analog or digital filters for rejecting electrical supply line noise are widely used in medical monitoring equipment, such as electrocardiographs. The filter is tuned to the supply line frequency to remove the induced noise from the signal carried by the ECG cable connected to the patient electrodes.

A digital adaptive notch filter, as shown in FIG. 1, can be employed for noise rejection in medical monitoring equipment which digitizes the input signal. The digitized input signal with noise comes into one input of the filter and a reference signal at the frequency of the noise to be rejected is applied to a filter control input. If the notch filter is incorporated in equipment for use in the United States, a 60 Hz sinusoidal reference signal is employed to tune the filter to the 60 Hz electrical supply line frequency. In other parts of the world where the electrical supply line frequency is 50 Hz, a reference signal at that frequency controls the tuning of the adaptive digital notch filter.

Although the electrical supply line frequency is maintained very accurately in the United States, in other parts of the world, that frequency varies widely from the nominal 50 Hz or 60 Hz. In some European countries, the line frequency can vary ±3 Hz from the 50 Hz nominal frequency. Thus if the noise filter tuning is fixed to the nominal electrical supply line frequency during manufacture, drifting of the electrical line frequency away from the nominal frequency results in the filter becoming ineffective or at least inefficient.

The obvious solution to this frequency drift problem is to make the notch of the filter wide enough to encompass the range of electrical supply line frequency deviation. However, this has the drawback in that the filter will remove a significant amount of the ECG signal spectrum thereby affecting operation of the medical monitor. Another obvious alternative is to adjust the tuning of the adaptive filter to variations in the electrical supply line frequency. This alternative requires additional detection circuits connected to the electrical supply line thereby adding cost to the medical monitor. Furthermore, in portable battery powered medical monitors, there is no way to directly sense the frequency of current in the adjacent electrical supply lines which still induce noise into the monitor input cable.

Therefore, it is desirable to be able to recover the electrical supply line frequency from the medical monitor input signal which contains both the patient signal and the supply line noise. The electrical supply line noise has a prominent presence in this input signal which makes the obvious approach to identify the supply line noise sinusoid in that composite signal and measure its period. However, a typical ECG digitizes the input signal with an analog to digital converter having a relatively low sampling frequency, 240 Hz for example. Unless a significantly faster, and more expensive, analog to digital converter is employed, recovery of the line noise frequency from the digitized input signal will be prone to a large measurement error.

For example, an analog to digital converter operating at 240 Hz has a sampling period of approximately 4.2 milliseconds. A 50 Hz electrical noise has a period of 20 milliseconds. Thus from samples of a 50 Hz noise signal taken at 4.2 millisecond intervals, a determination can be made that one cycle of the noise signal lasted somewhere in the 16.8 millisecond to 21 millisecond interval. However, this sampling procedure cannot determine more precisely where in that interval the electrical cycle ended. As a consequence, the same determination will be reached when the actual supply line frequency drifts anywhere between 46.6 Hz (1/(21 msec.)) and 59.5 Hz (1/(16.8 msec.)). The error range of this determination is 12.9 Hz. Therefore, in this typical medical monitor, the frequency of the noise cannot be determined directly from the conventional digital input signal data with any practical degree of accuracy.

As noted previously, a faster analog to digital converter capable of operating at a higher sampling frequency could be employed to narrow the range of sampling error. However, in order to obtain a measurement of the supply line frequency with an acceptable degree of accuracy, a relatively expensive analog to digital converter would have to be utilized. Therefore, it is desirable to derive the frequency of electrical supply line noise from a corrupted input signal utilizing as inexpensive and simple a circuit as possible.

SUMMARY OF THE INVENTION

A general object of the present invention is to provide a rejection filter for electrical supply line noise which is able to adapt to frequency variation of that noise.

Another object is to provide such an adaptive filter which does not require direct sensing of the electrical supply line frequency.

A further object of the present invention is to recover the electrical supply line frequency from an input signal which has been corrupted by supply line noise.

Still another object is to accomplish such recovery without employing a more expensive analog to digital converter than that otherwise utilized by the medical monitor.

Yet another object of the present invention is to provide such a filter with a narrow notch, so that only a negligible portion of the signal corrupted by the electrical line noise will be removed by the filter.

BRIEF DESCRIPTION OF THE DRAWINGS

FIG. 1 is a block diagram of an adaptive notch filter system according to the prior art; and FIG. 2 is a block diagram of an adaptive digital notch filter with a line frequency recovery circuit according to the present invention.

DETAILED DESCRIPTION OF THE INVENTION

In order to understand the approach taken by the present invention, consider a simple trigonometric equation:

$$\sin \alpha \cdot \sin \beta = \tfrac{1}{2} \cos(\alpha-\beta) - \tfrac{1}{2}\cos(\alpha+\beta) \qquad (1)$$

If $\alpha$ is replaced with $\omega_n t$ where $\omega_n$ represents the supply line frequency and t is time, and $\beta$ is replaced with $\omega_r t$ where is $\omega_r$ is the reference frequency of the adaptive filter, equation (1) becomes:

$$\sin \omega_n t \cdot \sin \omega_r t = \tfrac{1}{2} \cos(\omega_n-\omega_r)t - \tfrac{1}{2}\cos(\omega_n+\omega_r)t \qquad (2)$$

From the latter equation, it is seen that multiplication of two sinusoids produces a combination of the two sinusoids with terms representing the sum and difference of their frequencies. For example, multiplying a line noise sinusoid of 50 Hz by a specially created 45 Hz sinusoid, produces a combined signal which has two sinusoidal components, one at 95 Hz and another with a 5 Hz frequency. If the combined signal is sent through a low pass filter with a cutoff frequency of 50 Hz, the 95 Hz component will be removed leaving only the 5 Hz component. In this case, a 5 Hz signal period corresponds to 48 digitized signal samples (240/5) where the sampling frequency was 240 Hz. If the end of an electrical supply line cycle is found somewhere between the 48th and 49th sample, the frequency of that sinusoid will appear to be somewhere between 4.8979 Hz and 5.0 Hz. Then, to complete the recovery of the supply line frequency, the specially created value of the 45 Hz reference signal is added to the value of the frequency of the output from the low pass filter which results in a signal having a frequency of between 49.8979 Hz and 50.0 Hz which has a maximum error of only 0.1021 Hz. This potential error is two orders of magnitude less than the 12.9 Hz error produced by direct recovery from the 240 Hz sampled signal data.

FIG. 2 shows circuitry 10 that implements this approach for recovering the electrical supply line frequency from an input signal which has been corrupted with supply line noise. It is understood that the illustrated processing blocks may be implemented by individual digital circuits, but preferably are implemented by software executed by an existing microcomputer in the medical monitor, thus avoiding a need for additional components. The signal containing the medical monitor sensor signal and noise is applied to an input 12 of an analog to digital converter (ADC) 14, having a sampling frequency of 240 Hz, for example. The ADC 14 produces a stream of data values representing the analog input signal. The digitized output signal from the ADC 14 is applied via node 15 to one input of a digital multiplier 16 which has a second input connected to the output of a reference frequency generator 18. The reference frequency generator 18 produces a digital output signal that has a frequency which is 5 Hz less than the 50 Hz or 60 Hz supply line frequency.

For simplicity, operation of the supply line frequency recovery circuit 10 will be described with respect to a medical monitor for use at a location where the nominal electrical supply line frequency is 50 Hz. In that situation, the reference frequency generator 18 produces a 45 Hz sinusoidal digital data stream which is applied to the second input of the multiplier 16. The multiplier 16 produces a resultant digital signal on line 22 that is the product of those input signals and which contains sum and difference components (e.g. 5 Hz and 95 Hz) of the two input signal frequencies.

That resultant digital signal is supplied to a low pass filter 24 having a cutoff at the nominal supply line frequency, 50 Hz for example. The low pass filter removes the frequency sum component (e.g. 95 Hz) from the resultant digital signal so that the output signal on line 26 contains only the component corresponding to the frequency difference (e.g. 5 Hz) between the two input signals to multiplier 16. Any deviation of the electrical supply line from the nominal frequency produces a corresponding deviation of the frequency of the output signal from the low pass filter 24. One skilled in the art will appreciate that the cutoff frequency of low pass filter 24 may be set at any point that removes the frequency sum component from the resultant signal produced by multiplier 16. Thus, a fixed 50 Hz or 60 Hz cutoff may be used regardless of the nominal frequency of electric current in a particular country.

The filtered digital signal on line 26 is applied to an input of a period calculator 28 which analyzes the resulting filtered waveform and calculates the distance in terms of the number of samples between peaks of that waveform. In other words, the period calculator locates a first sample in the digitized data on line 26 which has a maximum value (a peak) among a given number of consecutive data samples. From that first sample, the period calculator 28 counts signal samples until it finds another maximum signal sample corresponding to the next peak in the signal. The number of signal samples counted between those signal peaks corresponds to the period of the difference signal on line 26. The signal period, in terms of a count of periodically sampled digital data samples, is applied to a period averager 30 which averages a plurality of the period counts. This averaging removes the effects of outliers which occur when the reference frequency is multiplied by QRS waveform fragments of an ECG signal when the signal to noise ratio is high.

The average number of samples within the signal period then is divided into the sampling rate (e.g. 240 Hz) of the analog to digital converter 14 by a divider circuit 32 to calculate a digital value representing the frequency of the difference signal. In the example being used to describe the present invention, the output of divider 32 will be somewhere around 5 Hz depending upon the exact frequency of electrical supply line noise. This derived value of the difference signal frequency is summed in adder 20 with a digital number on line 33 that indicates the reference frequency (e.g. 45 Hz) to obtain a digital value on line 34 denoting the noise frequency.

The digital value of the noise frequency is used by a line noise frequency generator 36 to generate a digital sinusoid signal which controls an adaptive digital notch filter 38. This digital sinusoid signal tunes a notch of the adaptive digital notch filter 38 to the instantaneous frequency of the electrical supply line noise thereby accounting for any drift from the nominal line frequency (e.g. 50 Hz). Thus the adaptive digital notch filter 38 can have a very narrow notch because the center frequency of the notch is varied in correspondence with drifting of the electrical supply line frequency and the induced noise.

The signal input for the adaptive digital notch filter 38 is connected to input node 15 and receives the digitized medical monitor input signal which has been corrupted with the electrical supply line noise. The adaptive digital notch filter 38 removes that noise from the input signal and provides a filtered signal at output 40 which is supplied to the remaining circuitry of the medical monitor. For example, in the case of an ECG, the signal at output 40 would represent the cardiac waveform to be evaluated.

In addition, the digital reference frequency produced by generator 18 is corrected utilizing the output of adder 20 to compensate for drift of the electrical supply line frequency. Specifically, the calculated noise frequency value from the adder 20 is applied to a subtractor 42 which subtracts a fixed 5 Hz value therefrom. In the exemplary circuit, the output of adder 20 will be 50 Hz, when the electrical supply line frequency has its nominal value (e.g. 50 Hz) thereby yielding a value corresponding to 45 Hz at the output of subtractor 42. Should the electrical supply line frequency deviate from that nominal value, the output from adder 20 will indicate that deviation. The output value from the subtractor 42 is applied to a control input of the reference frequency generator 18 and designates the frequency that the generator should produce. Thus, if the supply line frequency gradually increases, the digital reference signal frequency produced by generator 18 will follow that increase to maintain a small frequency difference (i.e. 5 Hz) between the noise signal and the reference signal. The smaller this corresponding difference, the larger the period of the signal on line 26 corresponding to that difference and the greater the accuracy of recovery circuit 10.

I claim:

1. A filter system for removing electrical supply line noise at a first frequency from an input signal, said filter system comprising:

a generator which produces a reference signal having a second frequency;

an differential circuit connected to the generator to produce an intermediate signal having a frequency that corresponds to a difference between the first and second frequencies;

a signal combiner connected to the generator and to the differential circuit to produce a filter control signal which has a frequency that is a sum of the second frequency and the frequency of the intermediate signal; and a notch filter having inputs which receive the input signal and the filter control signal, and having a filter notch is tuned in response to the frequency of the filter control signal.

2. The filter system as recited in claim 1 wherein the differential circuit comprises:

a multiplier that multiples the input signal and the reference signal to produce a resultant signal; and a low pass filter connected to the multiplier to remove from the resultant signal a frequency component that corresponds to a sum of the first and second frequencies and thereby produce a filtered resultant signal.

3. The filter system as recited in claim 2 wherein the differential circuit further comprises:

a period calculator connected to the low pass filter which determines a period of the filtered resultant signal and produces a period measurement; and a signal converter connected to the period calculator and producing the intermediate signal which has the period determined by the period measurement.

4. The filter system as recited in claim 2 wherein the differential circuit further comprises:

a period calculator connected to the low pass filter which determines a period of the filtered resultant signal and produces a period measurement;

an averager which averages a plurality of period measurements from the period calculator to produce an average period value; and a signal converter connected to the averager and producing the intermediate signal which has the period determined by the per average period value.

5. The filter system as recited in claim 1 wherein the second frequency of the reference signal produced by the generator is varied in response to the filter control signal.

6. A filter system for removing electrical supply line noise at a first frequency from a signal, said filter system comprising:

a generator which produces a reference signal having a second frequency;

an arithmetic unit connected to the generator to produce an intermediate signal having a frequency component that corresponds to a difference between the first and second frequencies;

a period calculator which determines a period of the intermediate signal;

a signal converter connected to the period calculator which produces a sinusoidal signal having the period determined by the period calculator;

an adder connected to the generator and the signal converter and producing a filter control signal having a frequency that is the sum of the second frequency and the frequency of the intermediate signal; and a notch filter which receives the input signal and which has a filter notch that is tunes in response to a frequency of a signal applied to a control input of the notch filter, wherein the control input is connected to the adder and receives the filter control signal.

7. The filter system as recited in claim 6 wherein the period determined by the period calculator is an average of a plurality of measurements of the period of the intermediate signal.

8. The filter system as recited in claim 6 wherein the arithmetic unit comprises:

a multiplier that multiples the input signal and the reference signal to produce a resultant signal; and a low pass filter connected to the multiplier to remove from the resultant signal a frequency component that corresponds to a sum of the first and second frequencies.

9. The filter system as recited in claim 6 wherein the second frequency of the reference signal produced by the generator is controlled in response to the filter control signal.

10. The filter system as recited in claim 6 further comprising an arithmetic circuit which subtracts a predefined frequency signal from the filter control signal and wherein the second frequency of the reference signal produced by the generator is controlled in response to an output of the arithmetic circuit.

11. A filter system for removing electrical supply line noise at a first frequency from an input signal, said filter system comprising:

a generator which produces a reference signal having a second frequency;

a multiplier that multiples the input signal and the reference signal to produce a first intermediate signal;

a low pass filter connected to the multiplier to remove from the first intermediate signal a frequency component that corresponds to a sum of the first and second frequencies thereby producing a second intermediate signal;

a period calculator connected to the low pass filter which determines the period of the frequency of the second intermediate signal and producing a period measurement;

an averager which averages a plurality of period measurements produced by the period calculator to produce and average period value;

a signal converter connected to the averager and which produces a sinusoidal signal having the period determined by the period calculator;

an adder connected to the generator and the signal converter and producing a filter control signal with a frequency that is the sum of the second frequency and the frequency of the sinusoidal signal; and a notch filter receiving the input signal and having a filter notch that is tuned in response to a frequency of a signal applied to a control input of the notch filter, wherein the control input is connected to the adder and receives the filter control signal.

12. The filter system as recited in claim 11 further comprising an arithmetic circuit which subtracts a predefined frequency signal from the filter control signal to produce a reference frequency; and wherein the second frequency of the reference signal produced by the generator is altered in response to the reference frequency.

* * * * *